United States Patent [19]

Cotty

[11] Patent Number: 5,171,686
[45] Date of Patent: Dec. 15, 1992

[54] **USE OF NATIVE *ASPERGILLUS FLAVUS* STRAINS TO PREVENT AFLATOXIN CONTAMINATION**

[75] Inventor: Peter J. Cotty, New Orleans, La.

[73] Assignee: The United States of America as represented by the United States Department of Agriculture, Washington, D.C.

[21] Appl. No.: 442,885

[22] Filed: Nov. 29, 1989

[51] Int. Cl.$^5$ ............................................. C12N 1/14
[52] U.S. Cl. ..................................... 435/254; 435/915
[58] Field of Search ................................ 435/254, 915

[56] References Cited

PUBLICATIONS

Ehrlich, K., *Mycopathologia*, vol. 97, (1987), pp. 93–96.
Hesseltine et al., Proceedings, First U.S.–Japan Conference on Toxic Microorganisms, "Production of Various aflatoxins by Strains of the *Aspergillus flavus* Series", pp. 202–210, 1970.

*Primary Examiner*—Douglas W. Robinson
*Assistant Examiner*—Deborah K. Ware
*Attorney, Agent, or Firm*—M. Howard Silverstein; John D. Fado; Joseph A. Lipovsky

[57] ABSTRACT

Methods and compositions are provided for the control or prevention of aflatoxin contamination of agricultural commodities. Non-toxigenic strains of *Aspergillus flavus* are shown to inhibit aflatoxin production by toxigenic strains. Additionally, the non-toxigenic strains produce a factor in culture that alone inhibits aflatoxin production by toxigenic strains.

3 Claims, No Drawings

USE OF NATIVE *ASPERGILLUS FLAVUS* STRAINS TO PREVENT AFLATOXIN CONTAMINATION

BACKGROUND OF THE INVENTION

1. Field of the Invention

This invention relates to a method for the control or prevention of aflatoxin contamination of commodities using non-toxigenic strains of *Aspergillus flavus* (*A. flavus*).

2. Description of the Prior Art

Aflatoxins are toxic compounds produced by fungi, particularly *A. flavus* and *Aspergillus parasiticus* (*A. parasiticus*), and are potent carcinogens that frequently contaminate agricultural commodities, especially during drought conditions, and are a serious threat to humans and animals [Cast, Counc. Agric. Sci. Technol. Rep., Vol. 80, (1979), Ames, IA., 56 pp]. The United States and most other countries prohibit aflatoxin levels in foods and feeds above 0.02 µg/g (20 parts per billion) Schuller, et al., Proceedings of the International Symposium on Mycotoxins, 1983, pp. 111-129, Naguib, et al. (eds.), National Research Centre, Cairo. *A. flavus* produces aflatoxins $B_1$ and $B_2$ and is the primary cause of aflatoxin contamination of corn, cottonseed, and tree nuts [Diener, et al., Annu. Rev. Phytopathol., Vol. 25, (1987), pp. 249-270].

There are several instances where a plant disease problem can be prevented by forms of the organism that incites the problem. Frost injury to plants results from ice formation caused by ice nucleation-active strains of *Pseudomonas syringae* and *Erwinia herbicola*; strains of these bacteria that are not ice nucleation active can be used to competitively exclude ice nucleation active strains and thereby prevent frost injury (Lindow, S.E., Appl. Environ. Microbiol., Vol. 53, pp. 2520-2527). Several viral diseases of plants are managed by infecting the plants with mild strains of the inciting viruses; through cross protection, plants infected with the mild strains are protected from infection by more severe strains [Yeh, et al., Plant Dis., Vol. 72, (1988), pp. 369-460]. Nonpathogenic strains of *Fusarium oxysporum* can prevent infection of celery by pathogenic strains through competitive exclusion [Schneider, R. W., Phytopathology, Vol. 74, (1984), pp. 646-653].

Cottonseed becomes contaminated with aflatoxins mainly following infection of pink bollworm-damaged bolls by *A. flavus* [Ashworth, et al., Phytopathology, Vol. 56, (1971), pp. 1104-1105 and Lee, et al., Plant Dis., Vol. 71, (1987), pp. 997-1001].

Currently tests are available that determine the presence and amount of aflatoxin; however, there are no methods on the market for the prevention of large scale crop loss due to accumulation of unacceptable levels of aflatoxin.

It is an object of the present invention to provide methods for prevention of the accumulation of aflatoxins in agricultural commodities.

SUMMARY OF THE INVENTION

Certain strains of *A. flavus* produce little or no aflatoxin and yet are highly aggressive. These strains are effective agents for the prevention of aflatoxin contamination in commodities.

It has been found that aflatoxin production by *A. flavus* is not required for infection of host tissues; furthermore, the ability to produce aflatoxins does not increase virulence of *A. flavus*. Therefore, aggressive strains which produce no aflatoxins should be able to competitively exclude toxigenic strains. Isolated non-toxigenic strains of *A. flavus* which occur naturally in agricultural fields have been found effective in preventing aflatoxin contamination by toxigenic strains.

Agricultural commodities inoculated simultaneously with both a non-toxigenic strain and a toxigenic strain produce seed with up to 100-fold less aflatoxin than commodities inoculated with a toxigenic strain alone. Non-toxigenic strains are even more effective at limiting aflatoxin contamination when inoculated prior to a toxigenic strain. Inhibition of aflatoxin production by non-toxigenic strains in culture is similar to the inhibition observed in vivo. Strain behavior in culture shows that non-toxigenic strains can directly inhibit aflatoxin production by toxigenic strains and that this inhibition is affected through evolution of one or more substances inhibitory to toxigenesis.

DETAILED DESCRIPTION OF THE INVENTION

EXAMPLE 1

Fungal Strains and Growth Conditions

Seventy strains of *A. flavus* were isolated from agricultural soil and cottonseed collected from Arizona desert valleys and sorted into two distinct strains on the basis of sclerotial size, cultural characteristics, and virulence to cotton. Strain L isolates produced large sclerotia (over 400 µm) whereas strain S isolates produced small sclerotia (less than 400 µm). Strain S isolates produced greater quantities of sclerotia in a wider assortment of media and a broader temperature range than strain L isolates. Isolates of both strains exhibited pH homeostasis in culture, however, the strains maintained different pH values.

Strain S isolates produced greater aflatoxin levels than strain L isolates in culture, however, strains S and L produced similar aflatoxin levels in vivo. Strain L isolates were more aggressive than strain S isolates at deteriorating locks and spreading within bolls and this tendency partly explained differences between aflatoxin production in vitro and in vivo. Aflatoxin levels in infected seeds did not correlate with either aflatoxin level in vitro, intra-boll fungal spread, or lock deterioration. Aflatoxin levels in infected seeds were correlated with the product of the aflatoxin level in vitro and the intra-boll spread parameter ($r=0.75$ to $0.91$). The correlation increased slightly ($r=0.78$ to $0.93$) when lock deterioration was factored into the equation. Results indicate that pathogenic aggressiveness contributes to isolate ability to contaminate cottonseed with aflatoxins. Lack of correlation between pathogenic aggression and aflatoxin production in vivo suggests aflatoxin does not enhance virulence in the cotton/*A. flavus* interaction.

Isolate origins are described in Table 1.

TABLE 1

Origins and sclerotial characteristics of *Aspergillus flavus* isolates.

| Isolate[d] | Origin[a] Crop | Origin[a] Substrate | Origin[a] Locale | Sclerotial diameters (μm)[b] Sample Size | Sclerotial diameters (μm)[b] Average | % over 400 μm | Sclerotial Production[c] 25° C. | Sclerotial Production[c] 30° C. | Sclerotial Production[c] 38° C. |
|---|---|---|---|---|---|---|---|---|---|
| 24 S | Alf | Soil | NGV | 192 | 250 ± 42 | 0 | M | M | M |
| 69 S | | | | 132 | 235 ± 49 | 0 | M | M | M |
| 37 S | | | SGV | 104 | 212 ± 55 | 0 | M | M | M |
| 61 L | | | | 91 | 481 ± 109 | 82 | 2 | 4 | 0 |
| 10 S | | | YV | 117 | 217 ± 51 | 0 | M | M | M |
| 18 S | | | | 90 | 199 ± 40 | 0 | M | M | M |
| 33 S | | | | 219 | 196 ± 43 | 0 | M | M | M |
| 19 L | BG | Soil | YV | 125 | 505 ± 119 | 82 | 1 | 3 | 0 |
| 5 S | | | | 274 | 211 ± 47 | 0 | M | M | M |
| 21 L | | | | 20 | 325 ± 64 | 10 | 0 | 1 | 0 |
| 23 L | | | | 62 | 543 ± 101 | 92 | 1 | 2 | 0 |
| 26 S | | | | 405 | 184 ± 37 | 0 | M | M | M |
| 60 L | | | | 54 | 514 ± 82 | 94 | 2 | 3 | 0 |
| 65 S | | | | 163 | 191 ± 38 | 0 | M | M | M |
| 66 S | | | | 167 | 189 ± 41 | 0 | M | M | M |
| 20 S | Cit | Soil | NGV | 141 | 210 ± 54 | 0 | M | M | M |
| 25 S | | | | 480 | 238 ± 62 | 0 | M | M | M |
| 27 S | | | | 190 | 243 ± 43 | 0 | M | M | M |
| 39 L | | | | 61 | 436 ± 67 | 75 | 2 | M | 0 |
| 7 S | | | YV | 107 | 200 ± 45 | 0 | M | M | M |
| 13 L | | | | 50 | 548 ± 103 | 94 | 0 | 2 | 0 |
| 15 S | On | Soil | NGV | 268 | 216 ± 51 | 0 | M | M | M |
| 59 S | | | | 148 | 209 ± 41 | 0 | M | M | M |
| 31 S | | | YV | 127 | 239 ± 43 | 0 | M | M | M |
| 46 S | | | | 220 | 203 ± 44 | 0 | M | M | M |
| 63 L | | | | 44 | 670 ± 110 | 98 | 0 | 4 | 0 |
| 64 L | | | | 80 | 486 ± 79 | 86 | 0 | 2 | 0 |
| 68 L | | | | 54 | 554 ± 108 | 91 | 2 | M | 0 |
| 1 L | PC | Soil | YV | 10 | 650 ± 92 | 100 | 1 | 1 | 0 |
| 6 L | | | | 61 | 603 ± 108 | 93 | 1 | 2 | 0 |
| 55 L | | | | 46 | 451 ± 89 | 67 | 2 | 3 | 0 |
| 70 S | | | | 159 | 163 ± 31 | 0 | M | M | M |
| 35 L | UC | Seed | MC | 77 | 396 ± 93 | 49 | 3 | M | 0 |
| 16 L | | | | 86 | 542 ± 108 | 92 | 0 | 1 | 0 |
| 17 L | | | | 47 | 691 ± 103 | 96 | 0 | 3 | 0 |
| 38 L | | | | 63 | 433 ± 57 | 65 | 3 | M | 0 |
| 41 L | | | | 101 | 447 ± 82 | 73 | 1 | M | 0 |
| 43 L | | | | 87 | 471 ± 76 | 82 | 4 | M | 0 |
| 45 L | | | | 47 | 447 ± 121 | 62 | 2 | 4 | 0 |
| 47 L | | | | 50 | 549 ± 61 | 98 | 2 | 4 | 0 |
| 48 L | | | | 88 | 431 ± 75 | 70 | 4 | M | 0 |
| 49 L | | | | 57 | 549 ± 77 | 98 | 0 | 4 | 0 |
| 51 L | | | | 2 | 480 ± 21 | 100 | 0 | 1 | 0 |
| 52 L | | | | 67 | 493 ± 96 | 84 | 2 | 4 | 0 |
| 53 L | | | | 73 | 409 ± 75 | 58 | 0 | 1 | 0 |
| 56 L | | | | 58 | 548 ± 81 | 97 | 1 | 3 | 0 |
| 57 L | | | | 60 | 628 ± 82 | 98 | 0 | 1 | 0 |
| 28 L | | | YV | 3 | 821 ± 91 | 100 | 0 | 1 | 0 |
| 29 S | | | | 134 | 211 ± 43 | 0 | M | M | M |
| 36 L | | | | 16 | 503 ± 117 | 75 | 1 | 4 | 0 |
| 40 L | | | | 70 | 506 ± 126 | 80 | 2 | 4 | 0 |
| 42 S | | | | 170 | 281 ± 36 | 0 | M | M | M |
| 50 L | | | | 74 | 521 ± 71 | 95 | 4 | M | 0 |
| 54 L | | | | 25 | 692 ± 130 | 92 | 1 | 2 | 0 |
| 58 S | | | | 342 | 263 ± 47 | 0 | M | M | M |
| 2 L | | Soil | NGV | 125 | 515 ± 103 | 89 | 2 | 4 | 0 |
| 3 S | | | YV | 127 | 193 ± 59 | 0 | M | M | M |
| 4 L | | | | 131 | 433 ± 52 | 73 | 2 | 2 | 0 |
| 8 L | | | | 90 | 466 ± 83 | 79 | 2 | 1 | 0 |
| 9 L | | | | 36 | 595 ± 130 | 94 | 0 | 3 | 0 |
| 11 L | | | | 52 | 642 ± 102 | 98 | 0 | 1 | 0 |
| 12 S | | | | 156 | 217 ± 49 | 0 | M | M | M |
| 22 L | | | | 147 | 488 ± 147 | 80 | 0 | 1 | 0 |
| 34 L | | | | 55 | 430 ± 121 | 53 | 2 | 4 | 0 |
| 30 S | | | | 115 | 200 ± 53 | 0 | M | M | M |

[a]Alf = alfalfa; BG = bermuda grass; Cit = citrus; On = onion; PC = Pima cotton; UC = upland cotton; NGV = North Gila Valley; SGV = South Gila Valley; YV = Yuma Valley; MC = Maricopa County.
[b]Silhouette areas were measured by video image analysis; average diameters were calculated from the areas by assuming spherical sclerotia. Avg. ± standard deviation.
[c]Sclerotia/plate after 12 days on Czapek solution agar with 3% $NaNO_3$. 1 = 1–50; 2 = 50–100; 3 = 200–400; 4 = 500–1000; M > 1000.
[d]Isolate numbers are followed by letters which denote the strain designation.

All isolates examined produced sclerotia in culture. For convenience, isolates producing numerous small sclerotia were designated strain S isolates [S=small, synonymous with the atypical strains of Saito, et al., Proc. Jpn. Assoc. Mycotoxicol., Vol. 24, (1986), pp. 41–46]; isolates with sclerotia greater than 400 μm dia. were designated strain L isolates (large). Soil isolates were obtained on a dichloran-amended medium by the dilution plate technique, Bell, et al., Phytopathology, Vol. 57, (1967), pp. 939–941, incorporated herein by reference. Distinct colonies were transferred to 5/2 agar (5% V-8 vegetable juice, 2% agar, adjusted to pH 5.2 prior to autoclaving) and utilized directly in the studies. Seed isolates were obtained on 5/2 agar either directly from the lint or from pieces of manually delinted seed disinfected for 2 m with 95% ETOH; seed isolate stock cultures originated from single spores. Fungi were maintained in the dark on 5/2 agar at 25° C. to 30° C.

To further characterize strains, their sclerotial characteristics were studied. Conidial suspensions (10 $\mu$l) were seeded into centers of Petri dishes (9 cm dia.) containing 30–35 ml Czapek solution agar (CZ) with 3% $NaNo_3$ and incubated at either 25° C., 30° C., or 38° C. for twelve days in the dark. Temperatures were maintained within one degree. Subsequently, conidia were washed from plates with 95% ETOH and the number of sclerotia per plate was estimated: 0=no sclerotia, 1=1 to 20, 2=50 to 100, 3=200 to 400, 4=500–1000, M=greater than 1000. Each test evaluated 5 to 12 isolates and isolates were tested one to four times.

Diameters of sclerotia produced on CZ with 3% $NaNO_3$ at 30° C. were determined by video-image analysis. Conidia were washed from plates with 95% ETOH and sclerotia were dislodged with a spatula and fixed in ethanol: glacial acetic acid (1:1 v/v). This procedure reduced human exposure to conidia. Sclerotia were blotted dry and stuck to clear plastic plates with two sided tape. Sclerotial silhouette areas were determined by video image analysis and diameters were calculated assuming spherical sclerotial shape.

Strains 42 and 13 produced large quantities of aflatoxins both in culture and during infection of developing cottonseed. Of all the strains studied, only strains 19, 36, 40, 51, 53, 55, and 63 produced levels of aflatoxin below the limit of detection of the assay employed (10 ng/g) [Cotty, P. J., Appl. Environ. Microbiol., Vol. 54, (1988), pp. 274–276, incorporated herein by reference].

These strains were tested as agents directed towards preventing contamination by toxigenic strains. Active cultures of all strains were maintained in the dark at 30° C. on 5% V-8 vegetable juice, 2% agar (Cotty, P. J., Ibid.). For long term storage, plugs (3 mm dia.) of sporulating cultures were maintained in 4-dram vials containing 5 ml of distilled water and refrigerated at 8° C. [Cotty, P. J., Plant Disease, Vol. 73, (1989), pp. 489–492, incorporated herein by reference].

EXAMPLE 2

Infection of Developing Cottonseed

Plants of Gossypium hirsutum cultivar Deltapine 90 were grown in a greenhouse in 3 liter pots containing a 50:50 mixture of Pro-mix (Premier Brands Inc., New Rochelle, N.Y. 10801) and sand (Cast, Ibid.). After three weeks, plants were fertilized weekly with 100 ml of 2,000 ppm Miracle-Gro (Sterms Miracle-Gro Products, Inc., Port Washington, N.Y.). Plants were maintained at all times in complete randomized blocks. Twenty-nine to 31 days after anthesis, developing cotton bolls were wounded once in a single lock with a cork borer (3 mm dia.) to simulate pink bollworm damage [Lee, et al., Plant Dis., Vol. 71, (1987), pp. 997–1001, incorporated herein by reference].

In most experiments bolls were inoculated with either approximately 20,000 conidia of a single strain or 20,000 conidia of each of two strains. For other treatments, wounds inoculated with one strain were subsequently (after 24 hr) inoculated with 20,000 conidia of a second strain. In one experiment, wounds were first inoculated with 2,000 conidia of a toxigenic strain and then inoculated in the same wound site after various periods (2, 4, 8, or 16 hr) with 20,000 conidia of a non-toxigenic strain. Bolls were harvested after maturation (3 weeks after inoculation) and dried at 60° C. for 2 days. Bolls were kept in a desiccator until analyzed for aflatoxin content. Experiments were replicated 3 to 8 times; replicates consisted of one to two plants. Experiments were performed in duplicate.

EXAMPLE 3

Aflatoxin Analyses

The in vivo aflatoxin content of intact inoculated locules was determined by a modification of the method of the Association of Official Analytical Chemists, Stoloff, et al., Official Methods of Analysis of the Association of Official Analytical Chemists, Williams, S. (ed.), Arlington, Va., 1984, pp. 477–500, incorporated herein by reference. Intact locks were hammered to pulverize the seed and added to 200 ml of acetone:water (85:15). The mixture was shaken for 15 mins, allowed to set overnight and filtered through number 4 Whatman paper. Twenty ml of a zinc acetate, aluminum chloride solution (1.1M $(CH_3COO)_2Zn$, 0.04M $AlCl_3$) was added with 80 ml water and 5 g diatomaceous earth to 100 ml filtrate. The mixture was shaken, left to settle for 1 to 2 hr, and passed through number 4 Whatman filter paper. Filtrate (100 ml) was extracted twice with 25 ml methylene chloride. Fractions were pooled and concentrated to dryness; residues were solubilized in methylene chloride and aflatoxin $B_1$ was separated and quantified by TLC (Stoloff, et al., Ibid.).

In vitro aflatoxin production was assessed qualitatively by seeding conidial suspensions (10 $\mu$l) in petri dishes (9 cm dia.) containing 30 to 35 ml of A&M agar [Mateles, et al., Appl. Microbiol., Vol. 13, (1965), pp. 208–211, incorporated herein by reference]. After ten days growth at 30° C. agar cultures were transferred to 250 ml jars with 25 ml acetone and shaken for 1 minute (min). Methylene chloride (25 ml) was added, the mixture was shaken for 1 min, filtered through 25 g sodium sulfate and the filtrate evaporated to dryness. Residues were solubilized in methylene chloride for thin layer chromatography (TLC). Extracts and aflatoxin standards were separated on TLC plates (silica gel 60, 250 $\mu$m thick) by development with diethyl ether-methanol-water (96:3:1, vol/vol/vol) and examined under ultraviolet light. Isolates negative for aflatoxin production in initial tests were grown on three plates containing A&M agar which were combined prior to extraction.

Quantitative estimates of aflatoxin production in vitro were made using the rapid fluorescence method. Culture tubes containing 5 ml of A&M agar were seeded with 100 $\mu$l spore suspensions containing approximately 100 spores/$\mu$l. After three days incubation at 30° C., agar fluorescence 5 mm beneath the mycelial mat was measured with a scanning densitometer. Agar fluorescence measured in this manner is directly correlated with the quantity of aflatoxin in the culture. Aflatoxin was extracted with solvents from representative tubes and quantified by thin-layer chromatography in order to construct a standard curve (fluorescence vs. toxin concentration) for each experiment (Cotty, P. J., Ibid.). Three experiments were performed containing 8, 24, and 44 isolates replicated 6, 7, and 4 times respectively.

Aflatoxin production in liquid fermentation was quantified by terminating fermentations with a volume of acetone equal to the initial volume of medium. This mixture was filtered after two hours, mixed with a volume of water equal to twice the initial volume of medium and extracted twice with 25 ml methylene chloride. The extract was dried and solubilized in methylene chloride for thin layer chromatography as described above.

EXAMPLE 4

Evaluation of Pathogenic Aggression

Intralock fungal spread was used as one measure of pathogenic aggression. During growth on cotton lint, *A. flavus* produces kojic acid which is converted by host peroxidase into a compound with bright-green-yellow-flourescence (BGYF) [Ashworth, et al., Phytopathology, Vol. 56, (1966), pp. 1104-1105]. Presence of BGYF on cotton lint is a reliable indicator of *A. flavus* activity (Ashworth, et al., Ibid.). Occurrence of BGYF on lint of uninoculated locks, therefore, was used to indicate fungal spread from inoculated to uninoculated locks. Uninoculated locks were examined under ultraviolet light after drying and BGYF on lint of each lock was rated: 0=none, 1=BGYF on less than 50% of the lint, 2=BGYF on more than 50% of the lint. The intra-boll spread parameter was the BGYF value; for correlations 0.1 was added to the BGYF value in order to compensate for the techniques low sensitivity and to avoid multiplying by zero.

After locks were dried, weights of inoculated and uninoculated locks were determined on a per lock basis. Weights were divided by the number of seeds within a given lock because the number of seeds per lock varied within bolls; inoculated lock weights were then divided by uninoculated lock weights to compensate for variance among bolls. For correlations the resulting value was subtracted from 1 and squared; this produced a value positively related to aggression.

Statistical Analysis. Analyses were performed using the Statistical Analysis System (SAS Institute, Inc., Cary, N.C.). All multiple comparisons were first subjected to analysis of variance. Toxin and fluorescence data were log transformed prior to analysis.

Pearson product-moment correlations were calculated for relationships between in vivo aflatoxin level and either in vitro aflatoxin level, intra-boll fungal spread, or lock deterioration; correlations between in vivo aflatoxin level and equations containing the three other parameters were also tested.

EXAMPLE 5

Results

Initial Comparisons of Isolates in Vivo. Large aflatoxin $B_1$ concentrations (5 to 152 $\mu$g/g) were produced in developing cottonseed by most isolates (Table 2).

One isolate, however, produced no aflatoxins in vivo and individual producing isolates varied significantly in the quantity of aflatoxins produced. Average aflatoxin levels produced by L and S strains in vivo were not significantly different (Table 2).

TABLE 2

Production of Aflatoxin B and BGYF by *Aspergillus flavus* isolates during boll infection and effect of infection on lock weight.

| Isolate[w] × 100 | Aflatoxin[x] ($\mu$g/g) | BGYF[y] | Inoculated lock weight Uninoculated lock weight |
|---|---|---|---|
| Test A | | | |
| 13 L | 152 ± 91[z] a | 1.11 ± 0.5 a | 47 ± 7 cd |
| 12 S | 119 ± 92 a | 0.26 ± 0.36 c | 57 ± 10 ab |
| 6 L | 101 ± 58 a | 0.93 ± 0.59 a | 49 ± 9 bcd |
| 11 L | 74 ± 36 a | 0.79 ± 0.68 a | 53 ± 7 abcd |
| 3 S | 38 ± 48 ab | 0.30 ± 0.57 bc | 57 ± 8 ab |
| 42 S | 27 ± 32 b | 0 ± 0 c | 55 ± 13 abc |
| 25 S | 8 ± 14 c | 0 ± 0 c | 62 ± 8 a |
| 36 L | 0 ± 0 d | 0.79 ± 0.65 ab | 45 ± 8 d |
| Average L | 82 ± 63 | 0.91 ± 0.15* | 49 ± 3* |
| Average S | 48 ± 49 | 0.14 ± 0.16* | 58 ± 3* |
| Test B | | | |
| 70 S | 129 ± 56 a | 0.84 ± 0.49 c | 60 ± 8 bc |
| 65 S | 101 ± 56 ab | 0.64 ± 0.26 c | 61 ± 6 b |
| 60 L | 59 ± 29 bc | 0.88 ± 0.44 bc | 56 ± 7 bc |
| 58 S | 44 ± 29 c | 0.19 ± 0.22 d | 63 ± 7 ab |
| 41 L | 43 ± 20 c | 0.88 ± 0.21 bc | 55 ± 7 bc |
| 16 L | 40 ± 27 c | 1.18 ± 0.26 ab | 52 ± 6 c |
| 54 L | 39 ± 22 c | 1.24 ± 0.19 a | 56 ± 4 bc |
| 66 S | 5 ± 4 d | 0 ± 0 d | 70 ± 5 a |
| Average L | 45 ± 9 | 1.05 ± 0.19* | 55 ± 3* |
| Average S | 60 ± 56 | 0.42 ± 0.39* | 64 ± 5* |

[w]Isolate numbers are followed by letters which denote the strain.
[x]Aflatoxin B content of inoculated locks.
[y]Bright-green-yellow-fluorescence per uninoculated lock: 2 = over 50% fluorescent lint, 1 = under 50% fluorescent lint, 0 = no fluorescence.
[z]Average ± standard deviation. Values within experiments with different letters differ significantly (P = 0.05) by Fischer's LSD test. * = L and S means differ significantly (P = 0.01) by Student's T-test.

Pathogenic aggression varied significantly both among isolates and between strains (Table 2). BGYF on lint of uninoculated locks, an indication of intra-boll fungal spread, was significantly greater in bolls inoculated with L strain isolates than in bolls inoculated with S strain isolates. L isolates also caused significantly larger reductions in inoculated lock weights than S isolates (Table 1). The two pathogenic aggression measurements were significantly correlated with each other (r = −0.85 to −0.89).

Aflatoxin levels in vivo did not correlate with aflatoxin levels in vitro (Table 3).

Similarly, aflatoxin levels in vivo correlated with neither intra-boll fungal spread nor inoculated lock deterioration. Aflatoxin levels in vivo were, however, correlated (r=0.75 to 0.91) with the products of the intra-boll spread parameter and the aflatoxin level in vitro; factoring in the lock deterioration parameter slightly improved the correlation (r=0.78 to 0.93) (Table 3). The strain which produced no toxins in vivo, strain 36, was highly aggressive at infecting cotton bolls as indicated by both measures of pathogenic aggression.

TABLE 3

Correlation coefficients and probabilities of correlations between in vivo aflatoxin level and various parameters.

| Parameter correlated with in vivo toxin[a] | Test 1 r | Test 1 P | Test 2 r | Test 2 P |
|---|---|---|---|---|
| A: In vitro toxin | 0.3964 | 0.3309 | 0.4780 | 0.2309 |
| B: Lock deterioration | 0.2783 | 0.5045 | 0.1590 | 0.7069 |
| C: Intra-boll spread | 0.5298 | 0.1768 | 0.2560 | 0.5404 |
| D: A × B | 0.5064 | 0.2003 | 0.7262 | 0.0414 |
| E: A × C | 0.7530 | 0.0220 | 0.9101 | 0.0017 |

TABLE 3-continued

Correlation coefficients and probabilities of correlations between in vivo aflatoxin level and various parameters.

| Parameter correlated with in vivo toxin[a] | Test 1 r | Test 1 P | Test 2 r | Test 2 P |
|---|---|---|---|---|
| F: A · B · C | 0.7843 | 0.0204 | 0.9291 | 0.0008 |

[a] A = the quantity of toxin produced in culture medium during 3 days growth at 30°C.; B = [1 − (average inoculated lock weight/average uninoculated lock weight)]²; C = the average quantity of bright-green-yellow fluorescence on lint of uninoculated locks plus 0.1.

Inoculation of developing cotton bolls with toxigenic *A. flavus* strains 13 and 42 resulted in cottonseed with very high aflatoxin levels (Table 4); maximum average toxin levels ranged from 4 to 120 μg aflatoxin $B_1$/g cottonseed in the various experiments. When bolls were coinoculated with toxigenic and non-toxigenic strains in equal proportions, however, the quantities of aflatoxin $B_1$ in cottonseed at maturity were markedly reduced compared with toxin levels in cottonseed from bolls inoculated with the toxigenic strain alone. When coinoculated, non-toxigenic strain 36 prevented detectable aflatoxin production in developing cottonseed by toxigenic strain 42 and reduced production of toxin by strain 13 up to tenfold (Table 4).

Non-toxigenic strains were not equally effective at limiting contamination of developing cottonseed when coinoculated with toxigenic strain 13 (Table 5). Strain 36 was the most effective strain at limiting toxin production by strain 13 in developing cotton bolls. Several non-toxigenic strains of *A. flavus* from the culture collection at the Northern Regional Research Center were not effective in one test (Table 6). Whereas, strain 36 was effective in all tests. Strain 36 has been deposited in the Agricultural Research Service Culture Collection (NRRL) International Depositary Authority, 1815 N. University St., Peoria, Ill. 61604, U.S.A. under the terms and conditions of the Budapest Treaty on the International Recognition of the Deposit of Microorganisms for the Purposes of Patent Procedure and accorded the number NRRL 18543. The strain has been deposited as the best mode known to the inventor and not meant to limit the invention.

Inoculation of developing cotton bolls with strain 36 alone usually resulted in no aflatoxin in cottonseed at maturity. Low levels (>50 ng/g) of aflatoxin $B_1$, however, were occasionally detected in seed from bolls inoculated with non-toxigenic strain 36 alone. This was apparently attributable to cross contamination by a toxigenic strain either prior to or during inoculation.

TABLE 5

Effect of inoculation with various non-toxigenic strains of *Aspergillus flavus* on contamination of cottonseed produced in bolls inoculated with a toxigenic strain.[x]

| Nontoxigenic strain | Aflatoxin $B_1$ content of cottonseed (μg/g)[y] Test 1 | Test 2 |
|---|---|---|
| none | 128.0 a | 4.48 a |
| 53 | 70.0 a | 0.93 b |
| 51 | 40.1 ab | 0.53 b |
| 19 | 24.9 abc | 0.13 b |
| 55 | 13.3 abc | 0.12 b |
| 63 | 11.6 abc | 0.12 b |
| 40 | 6.5 bc | 0.12 b |
| 36 | 1.3 c | ND b |

[x]Developing cotton bolls were inoculated with toxigenic strain 13 and after 30 min reinoculated with equal inoculum of a non-toxigenic strain.
[y]Limit of detection 0.01 μg/g; ND = none detected. Means in the same test followed by the same letter do not differ significantly (P = 0.05) by Fishcher's least significant difference test. Data were transformed into logarithms to homogenize variances prior to analysis.

TABLE 6

Effect of inoculation with either non-toxigenic strain 36 or non-toxigenic strains from the Northern Regional Research Center culture collection on contamination of cottonseed produced in bolls inoculated with a toxigenic strain of *Aspergillus flavus*.

| Non-toxigenic strain | Aflatoxin $B_1$ content of cottonseed (μg/g) |
|---|---|
| none | 37.0 |
| 36 | 5.1 |
| NRRL 1957 | 85.5 |
| NRRL 5918 | 59.4 |
| NRRL 5565 | 37.8 |
| NRRL 5917 | 30.8 |

Developing cotton bolls were inoculated with toxigenic strain 13 and after 30 min reinoculated with equal inoculum of a non-toxigenic strain.

Inoculation of bolls with non-toxigenic strain 36 one day prior to inoculation with equal inoculum of toxigenic strains 13 and 42 resulted in almost complete prevention of seed contamination (Table 4). If bolls were inoculated with toxigenic strains one day prior to inoculation with strain 36, contamination was equal to inoculation with the toxigenic strains alone. This indicates that competitive exclusion may be an aspect of the activity of strain 36.

Bolls inoculated with toxigenic strain 13 and then inoculated in the same wound site with a tenfold inoculum concentration of strain 36 after various periods also frequently had reductions in aflatoxin levels compared to bolls inoculated with strain 13 alone (Table 7); the quantity of aflatoxin $B_1$ in cottonseed at maturity was significantly reduced when strain 36 was inoculated into bolls up to 16 hrs after inoculation with strain 13. This suggests that strain 36 may actively inhibit aflatoxin production by toxigenic strains in addition to competitively excluding them. This is also suggested by strain 36 exerting equal inhibitory effect when applied at concentrations either equal to or one half those of the toxigenic strain (Table 8).

TABLE 4

Aflatoxin content of cotton bolls inoculated with toxigenic and non-toxigenic strains of *Aspergillus flavus* individually and in combination.

| Strain | Toxigenicity | Aflatoxin $B_1$ content of cottonseed (μg/g)[x] Alone | Mixed with strain 36 | Inoculated 24 hr after strain 36 | Inoculated 24 hr before strain 36 |
|---|---|---|---|---|---|
| 13 | + | 72 w | 6 x | 0.4 z | 96 w |
| 42 | + | 17 y | ND z | ND z | 15 y |
| 36 | − | 0 z | | | |

[x]Limit of detection 0.01 μg/g; ND = none detected. Means throughout the table followed by the same letter do not differ significantly (P = 0.05) by Fischer's Least Significant Difference Test. Data were transformed into logarithms to homogenize variances prior to analysis. The experiment was performed twice with similar results. Results of a single test are presented.

TABLE 7

Effect of length of time prior to challenge with a non-toxigenic strain on contamination of developing cottonseed by a toxigenic strain of *Aspergillus flavus*.[x]

| Time between inoculation and challenge (hr) | Aflatoxin $B_1$ content of cottonseed[y] ($\mu g/g$) |
| --- | --- |
| 2 | 1.40 b |
| 4 | 1.51 b |
| 8 | 3.69 b |
| 16 | 6.89 b |
| no challenge | 30.35 A |

[x]Developing cotton bolls were inoculated with toxigenic strain 13 and reinoculated after various periods with a ten fold conidial concentration of non-toxigenic 36.
[y]Values are averages of eight observations made during two tests. Values followed by the same letter are not significantly different by the LSD test for split-plot analyses. Analyses were performed on ranks assigned to values within tests prior to analysis.

TABLE 8

Growth, toxin production and alteration of culture pH by two strains of *Aspergillus flavus* grown individually and in combination.

| Strain ratio[b] (13:36) | Aflatoxin $B_1$ $\mu g/g$ | | | Final pH[a] | | Fungal mass (g) | |
| --- | --- | --- | --- | --- | --- | --- | --- |
| | In vivo[c] | $NH_4$[d] | $NO_3$[d] | $NH_4$ | $NO_3$ | $NH_4$ | $NO_3$ |
| 1:0 | 501 | 445 | 213 | 2.34 | 6.10 | 0.48 | 0.38 |
| 0:1 | 0 | 0 | 0 | 2.28 | 5.96 | 0.43 | 0.45 |
| 1:1 | 8 | 30 | 3 | 2.30 | 5.71 | 0.50 | 0.54 |
| 2:1 | 7 | 45 | 9 | 2.24 | 5.68 | 0.52 | 0.53 |

[a]Final pH of the culture medium: initial pH was 5.0.
[b]Flasks containing 50 ml medium were seeded with 16 conidia/μl of either strain 13 which does not produce aflatoxins or strain 36 which does produce aflatoxins. For two treatments flasks which were seeded with strain 13 were also seeded with either 16 or 8 conidia/μl of strain 36. Flasks were incubated at 28° C. for 4 days prior to being extracted and analyzed for aflatoxin production. Values are averages of 4 replicates.
[c]Cotton bolls 28 to 30 days old were inoculated with about 3,000 conidia of either strain 13 or strain 36; plants in two treatments were inoculated with both strain 13 and either 3,000 or 1,500 conidia of strain 36. Plants were treated and analyzed for toxin content as described in Examples 3 and 4. Values are averages of 4 replicates.
[d]$NH_4$ = the A&M agar described in the text without agar; $NO_3$ = the $NH_4$ medium with 3 g $NaNO_3$ substituted for the $(NH_4)_2SO_4$. Aflatoxin is expressed as per gram mycelium.

Example 6

Field Delivery

Field delivery of non-toxigenic *A. flavus* strains was accomplished by the following protocol.

Whole red winter wheat was sterilized in an autoclave and then dried in a drying oven (60° C. for 2 days). The resulting wheat was placed in tissue culture roller bottles and inoculated with conidia of non-toxigenic strain 36 (approximately 200,000 spores per ml) in sufficient water to bring the moisture level of the wheat to 20%. The inoculated wheat was incubated at 28° C. on a roller drum at approximately five revolutions per minute for one week. At the end of this period the fungus grew in the fold of the seed and under the seed coat but, very few or no spores were produced.

When this seed is exposed to adequate humidity and temperature, the non-toxigenic strain produces numerous conidia until the nutrients in the wheat are depleted (in one test over 6 billion conidia per gram of wheat were produced in 10 days at 30° C. and 100% RH). Thus, when this formulation is delivered to the field and conditions favoring spread of *Aspergillus flavus* occur, the control agent (non-toxigenic strain 36) is released. Alternatively, the agent can be delivered in a liquid spray using conventional spray equipment and 0.01% Triton X-100 surfactant.

It is envisioned that any system for biocontrol delivery, known to the skilled artisan, can be used for the administration of non-toxigenic *A. flavus* strains to agricultural commodities either pre-or postharvest. Additionally, carrier agents for biocontrol can be inert compounds or compositions including stabilizers and preservatives known in the art.

Example 7

Involvement of Factors Elaborated by a Non-toxigenic Strain in Inhibition of Toxin Production by a Toxigenic Strain Strain 36 exerted a similar influence on toxin production by strain 13 both in culture and in infected plants (Table 8). Strain 36 inhibited aflatoxin production by strain 13 when either seeded into fermentation flasks or inoculated into developing cottonbolls. The level of inhibition was similar regardless of whether the inoculum of 36 was equal to the concentration of 13 or half the concentration of 13 (Table 8). This inhibition occurred both in $NH_4$ and $NO_3$ based media and is apparently independent of pH effects (Table 8).

Strain 36 exerted inhibition of aflatoxin production by strain 13 even when the two strains were grown separately and mixed after various periods. Mycelial balls were evident in liquid fermentation after just 10 hrs and after 48 hrs the initiation of toxin production by strain 13 was detected. Even when mycelial balls 48 hr old were mixed with an equal quantity of mycelial balls of strain 36, toxin production by strain 13 was significantly inhibited (Table 9). This suggests that inhibition of toxin production by strain 36 is through elaboration of an inhibitory factor.

Cell free filtrates of strain 36 were substituted for water in A&M medium (A&M agar without agar). Strain 13 produced significantly less aflatoxin in A&M medium made with filtrates of strain 36 than on A&M medium made with water. This is evidence that an extracellular factor inhibitory to aflatoxin production is produced by strain 36 (Table 10).

TABLE 9

Influence of non-toxigenic strain 36 on toxin production by toxigenic strain 13 when strains are cultured separately for 0 to 48 hr prior to mixing.

| Treatment[a] | Aflatoxin $B_1$ $\mu g/g$ mycelium[b] |
| --- | --- |
| Control 1 day | 0 |
| Control 2 day | 1.2 |
| Control 5 day | 138.5 |
| Mix 0 hr | 5.2 |
| Mix 5 hr | 0.5 |
| Mix 10 hr | 2.7 |
| Mix 24 hr | 22.8 |
| Mix 36 hr | 30.8 |

[a]Flasks containing 70 ml of the $NO_3$ medium described in Table A were inoculated with approximately 3,000 spores per ml of either toxigenic strain 13 or non-toxigenic strain 36. Flasks were shaken at 150 rounds per minute while incubating at 28° C. After various periods (2 to 48 hr) the contents of flasks containing strain 36 were mixed with the contents of flasks containing strain 13. The mixture was divided into 70 ml portions, incubated for the remainder of the 5 day incubation period and analyzed for aflatoxin content. Control flasks in which strain 13 alone was cultured for 1, 2 or 3 days were also analyzed for toxin. Values are averages of 4 replicates.

TABLE 10

Effect of cell-free filtrate of *Aspergillus flavus* strain 36 on toxin production by toxigenic strain 13.

| Treatment[a] | Aflatoxin $B_1$ ($\mu g/g$) | Aflatoxin $B_2$ ($\mu g/g$) | Total aflatoxins ($\mu g/g$) |
| --- | --- | --- | --- |
| Control | 184 | 23 | 207 |

TABLE 10-continued

Effect of cell-free filtrate of *Aspergillus flavus* strain 36 on toxin production by toxigenic strain 13.

| Treatment[a] | Aflatoxin $B_1$ ($\mu$g/g) | Aflatoxin $B_2$ ($\mu$g/g) | Total aflatoxins ($\mu$g/g) |
| --- | --- | --- | --- |
| Filtrate | 56 | 1 | 57 |

[a] A&M medium without agar was made with water as described in the text or with a cell free culture filtrate of strain 36 substituted for water. Flasks containing 70 ml of such media were inoculated with approximately 3,000 spores of strain 13 per ml, incubated at 28° C. for 5 days, and analyzed for aflatoxins. The cell-free filtrate was made by growing strain 36 in the $NO_3$ medium as described in Table A for 6 days; the filtrate was prefiltered with Whatman glass micro fibre filters and sterilized by passing through a 0.22 $\mu$m filter.

There has been provided in accordance with the present invention, a biocontrol agent, compositions, and methods for the prevention and/or control of aflatoxin contamination in agricultural commodities. It can be seen from the preferred embodiments that many variations and alternatives may be practiced without departing from the spirit and scope of the invention. It is intended that the scope of this invention includes such variations and alternatives.

I claim:

1. A biologically pure culture of *Aspergillus flavus* having the identifying characteristics of strain NRRL 18543, wherein said identifying characteristics include the ability to inhibit aflatoxin production by native aflatoxin producing strains of *Aspergillus flavus* and hence reduce aflatoxin contamination of agricultural commodities.

2. The biologically pure culture of claim 1, wherein the culture is suspended in a carrier agent.

3. The biologically pure culture of claim 2, wherein the carrier agent comprises an aqueous 0.01% w/v nonionic surfactant.

* * * * *